United States Patent [19]

Heino

[11] Patent Number: 5,607,671
[45] Date of Patent: Mar. 4, 1997

[54] MEDICAL USE, A MEDICAL METHOD AND A PHARMACEUTICAL PREPARATION

[76] Inventor: Pekka U. Heino, Lahnaruohontie 4 D 45, 00200 Helsinki, Finland

[21] Appl. No.: 256,508

[22] PCT Filed: Jan. 18, 1993

[86] PCT No.: PCT/FI93/00016

§ 371 Date: Sep. 14, 1994

§ 102(e) Date: Sep. 14, 1994

[87] PCT Pub. No.: WO93/13795

PCT Pub. Date: Jul. 22, 1993

[30] Foreign Application Priority Data

Jan. 17, 1992 [FI] Finland .................................. 920206

[51] Int. Cl.⁶ .......................... A61K 38/43; A61K 38/46; A61K 38/47; A61K 38/48
[52] U.S. Cl. ................... 424/94.1; 424/94.6; 424/94.61; 424/94.62; 424/94.63; 424/457; 514/198; 540/336
[58] Field of Search .................. 424/94.1, 94.6, 424/94.61, 94.62, 94.63, 457; 548/336; 514/198

[56] References Cited

FOREIGN PATENT DOCUMENTS

0420600A3  3/1991  European Pat. Off. .
WO88/07865 10/1988 WIPO .

*Primary Examiner*—John W. Rollins
*Attorney, Agent, or Firm*—Jacobson, Price, Holman & Stern, PLLC

[57] ABSTRACT

The invention concerns medical use, a medical method and a pharmaceutical preparation. The invention allows the action of β-lactam antibiotics to be targeted and their side effects to be reduced by inactivation of part of the antibiotic in a desired section of the digestive tract distal to the stomach by administering, separately from or simultaneously with antibiotic, and enzyme, such as β-lactamase, which breaks down said antibiotic.

21 Claims, No Drawings

MEDICAL USE, A MEDICAL METHOD AND A PHARMACEUTICAL PREPARATION

The present invention addresses all such antimicrobial therapy in man in which β-lactam antibiotics are the therapeutic agents.

The invention uses oral administration of enzymes to break down the therapeutically detrimental β-lactam antibiotic pool, which accumulates in the gut in conjunction with β-lactam antibiotic therapy, into compounds with little (low) or no antimicrobial activity, thus eliminating or diminishing the adverse microbiological effects otherwise encountered among the beneficial, normal bacterial flora of the body, especially in the gut.

The benefits of the invention can be directly availed of with conventional prevention and treatment regimes for bacterial diseases. The invention also allows higher single doses or prolonged administration of β-lactam antibiotics to be used in cases in which effective treatment has so far been hindered by the microbiological side effects of the antibiotic.

The invention also makes possible local antimicrobial therapy, e.g. for bacterial gastritis, gastric and duodenal ulcers, using oral administration of such β-lactam antibiotics which have so far been limited to the parenteral route of administration. Thus the potent antimicrobial properties of these antibiotics can be more extensively availed of.

β-lactam antibiotics are antimicrobial agents which destroy bacteria sensitive to β-lactam antibiotics. Their common feature is the β-lactam ring in their molecules (I):

$$\begin{array}{c} -CH-CH- \\ | \quad\quad | \\ O=C\!\!-\!\!-\!\!N- \end{array} \quad (I)$$

The β-lactam ring gives these compounds the antimicrobial property availed of in the treatment of bacterial diseases. All β-lactam antibiotics (henceforth β-LABs, AB for antibiotic) discovered in the period 1940–1970 belong to two structural classes: the penicillins (II), in which the β-lactam ring is fused with a thiazolidine ring, and the cephalosporins (III), in which the β-lactam ring is fused with a dihydrothiazine ring.

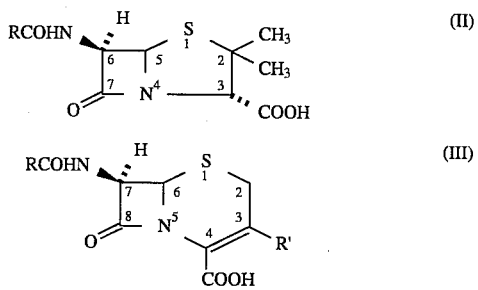

The more recently introduced compounds are known as nonclassic β-LABs. These include the carbapenems, in which the sulphur atom in the 1-position of the β-lactam nucleus of the penicillins is replaced by a carbon atom, and the monobactams, in which the β-lactam ring is not fused with any other ring structure at all.

With the exception of benzylpenicillin, which is prepared from natural sources, penicillins intended for clinical use are derived semisynthetically by attaching a desired side chain to the amino group of 6-aminopenicillanic acid, 6-APA (IV) (U.S. Pat. No. 2,941,995, U.S. Pat. No. 3,499,909). One method of penicillin preparation is to extract natural penicillins produced by various moulds and then remove the undesired side chains in the 6-position in these penicillins enzymatically using penicillin amidases (FI 59265) to obtain 6-APA, followed by incorporation of a new side chain in this position (GB 1241 844).

Cephalosporins are manufactured from 7-aminocephalosporanic acid (V) (U.S. Pat. No. 3,239,394), 7-ACA, a compound analogous with 6-APA, by linking requisite radicals to the amino group in the 7-position and sometimes even to the side chain in the 3-position.

The nonclassic β-LABs are isolated from natural microorganisms.

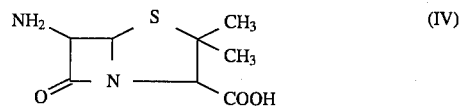

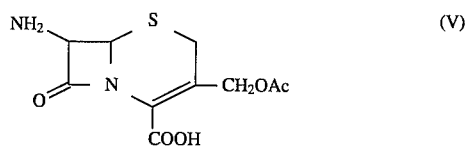

Neither of the above-mentioned compounds, 6-APA and 7-ACA, possess any antimicrobial potency of significance (Korzybski and Kurylowicz 1961, Huber et al. 1972).

The penicillin amidases used in the semisynthetic manufacture of β-LABs are a structurally heterogeneous group of enzymes produced by a wide range of microorganisms (US 3,150,059) and also by mammalian cells (U.S. Pat. No. 3,070,511 ). Their common feature is the ability to quite substrate-specifically hydrolyse the side chain of various penicillins. The side chains hydrolysed include acyl groups in the 6-position of the β-lactam nucleus and, in the case cephalosporins, acyl groups in the 7-position. The remaining compounds are 6-APA and 7-ACA (IV and V) with a an amino group in the 6- or 7-position, respectively. To recapitulate, the reaction is a case of hydrolysis of the amide bond of a side chain bound to the β-lactam ring with a linear amide bond.

Penicillin amidases are also called penicillin acylases, amino acid acylases or aminohydrolases. The International Enzyme Nomenclature places these enzymes in class 3.5.1.11 (EC 3.5.1.11).

β-LABs constitute the largest group of antimicrobial drugs available today.

The following penicillins, among others, have found use in the treatment of bacterial diseases: (1) benzylpenicillin (also known as penicillin G), (2) phenoxymethylpenicillin (also known as penicillin V), (3) ampicillin, (4) bacampicillin (an ester of ampicillin), (5) pivampicillin (an ester of ampicillin), (6) amoxicillin, (7) carbenicillin, (8) piperacillin, (9) phenethicillin, (10) propicillin, (11) methicillin, (12) nafcillin, (13) oxacillin, (14) cloxacillin, (15) dicloxacillin, (16) flucloxacillin, (17) epicillin, (18) cyclacillin, (19) ticarcillin, (20) temocillin, (21) azlocillin, (22) meziocillin.

Of the cephalosporins, at least the following are in clinical use: (23) cephalexin, (24) cephradine, (25) cefatrizine, (26) cefaclor, (27) cefroxadine, (28) cefadroxil, (29) cephaloglycin, (30) cephalothin, (31) cephapirin, (32) cephacetrile, (33) cephaloridine, (34) cefazolin, (35) cefuroxime, (36) cefamandole, (37) cefoxitin, (38) ceforanide, (39) cefonicid, (40) cefotaxime, (41) ceftizoxime, (42) cefoperazone, (43) ceftriaxon, (44) cefmenoxime, (45) keftazidime, (46) cefotiam, (47) cefodizime, (48) cefixime.

Further, (49) imipenem of the carbapenems and (50) azthreonam of the monobactams are in clinical use.

In addition to the above, several other β-LABs are currently in clinical use or undergoing clinical trials.

Below, when referring to one of the above-mentioned compounds, the compound number appearing in parentheses above or the name of the compound or both will be used.

β-LABs are administered either orally or parenterally. The latter method includes the intramuscular and intravenous routes.

Oral administration can be used when the β-LAB in question is absorbed in sufficient amounts from the intestine into the systemic blood circulation. These are accordingly known as oral β-LABs. The following of the compounds listed above are oral β-LABs: 2–6, 9, 10, 13–18, 23–29 and 48. Oral β-LABs can in most cases also be administered parenterally if required.

β-LABs must be administered parenterally in cases in which the particular compound used would not be sufficiently absorbed from the gastrointestinal tract. This may be due to the drug being completely or partly decomposed by the gastric juice excreted by the stomach. A number of penicillins (1, 7, 8, 11, 12, 19–22) belong to this category.

Another reason for parenteral administration is the fact that many β-LABs, though withstanding gastric juice, are negligibly absorbed from the intestines.

Most cephalosporins, carbapenems and monobactams are such parenteral β-LABs.

As examples of the percent intestinal absorption of the β-LABs may be mentioned those of penicillin V (2), 40–60%, ampicillin (3), 30–40%, bacampicillin (4), over 95%, amoxicillin (6), 60–70%, phenethicillin (9), 20–40% cephalexin (23), over 95%, cephradine (24), over 90%, cephaloglycin (29), 25%, cephalothin (30), 1–3%, cephaloridine (33), 1–4%, and other cephalosporins (31, 32, 34–47), imipenem (49) and azthreonam (50), 0–5%.

Any gastrointestinal absorption takes place almost exclusively in the duodenum and the proximal jejunum, which in terms of duration corresponds to 1–3 h. This is reflected in the emergence of the ingested β-LAB in the systemic circulation (plasma) within this period. Depending on the compound, the peak plasma concentration is usually reached within 1–2 h of the time of administration.

β-LABs that have reached the systemic circulation either through oral or parenteral administration are excreted mainly via the kidneys in the urine. Excretion usually takes place quite rapidly, the plasma halflife, calculated from the time of peak plasma concentration, being 0.5–2.0 h in nine out of ten β-LABs.

In the case of most penicillins, urinary excretion of the unchanged antibiotic is accompanied by excretion of its quantitatively most important metabolite, i.e. a penicilloic acid (VI) corresponding to the penicillin derivative used.

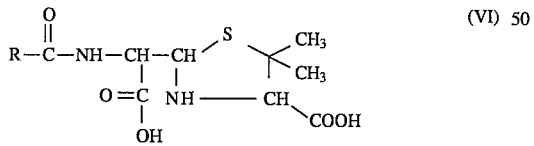

(VI)

In this compound, which for instance in the case of amoxicillin is the only known metabolite (accounting for 35% of the dose excreted in the urine), the β-lactam ring is open. This leads to disappearance of all the important antimicrobial properties seen in the original molecule. The same is true for all β-LABs.

In man, the conversion of cephalosporins into corresponding cephalosporanoic acids through cleavage of the β-lactam ring, a process analogous with that in penicillin metabolism, is nevertheless insignificant in amount and, thus, this route is not important in the metabolism of cephalosporins.

Those of the cephalosporins (29–32) in which the β-lactam nucleus carries in the 3-position a substituent containing an ester bond are metabolised to the corresponding deacetyl cephalosporins through enzymatic breakage of the ester bond. The deacetyl cephalosporins are excreted in the urine together with the unchanged cephalosporin. These metabolites possess an antimicrobial activity equivalent to or weaker than that of their parent compounds.

Other cephalosporins than 29–32 do not yield any significant urinary metabolites.

Imipenem (48) is more or less completely inactivated by cleavage of the β-lactam ring prior to urinary excretion of the metabolite in question. A few β-LABs are, in addition to urinary excretion, to a significant extent excreted unchanged in bile. This is the route of excretion for 20% of piperacillin (8), 30–40% of ceftriaxon (43) and over 80% of cefoperazone (42).

Ceftriaxon is exceptional in that the proportion excreted in bile is known to be broken down into inactive metabolites by the normal bacterial flora in the gut (Therapeutic Drugs 1991). As a rule, the intestinal flora does not, however, break down the β-LABs entering the gut. For example, in the case of ampicillin (3), which has long-established, extensive use as an orally administered antibiotic, a major part of the dose is excreted unchanged in the faeces (Mandell and Sande 1990).

Toxicologically, β-LABs are almost completely nontoxic, which is an essential asset compared with other antibiotics in clinical use. In addition to the β-LABs themselves, their major metabolites, such as the above-mentioned penicilloic acids, are nontoxic.

However, β-LAB metabolites with a cleaved β-lactam ring may (in contrast to intact β-LABs) give rise to allergic reactions in susceptible individuals. Such reactions occur in 0.7–10% of patients treated with penicillins. The corresponding figure for cephalosporins is 0.8–7.5%.

In the 1950s, at a time when the β-LABs in clinical use were still limited to a few penicillinic compounds, and the allergic reactions encountered in therapy were thought to be due to the intact penicillin molecule, trials were conducted with an enzyme, then known as penicillinase, which breaks penicillin down into penicilloic acid. The object was to investigate the therapeutic potential of this enzyme in the treatment of these, often severe, symptoms, using parenteral administration.

The trials yielded inconsistent results, and they were soon discontinued because of frequent allergic side effects, i.e. the very same symptoms which the trial therapy had sought to prevent (Hyman 1959).

The clinical manifestations of the allergic reaction are currently known to be caused by allergenic complexes formed in a reaction between native proteins of the body and open β-lactam nuclei (e.g. penicilloic acids). There is today no causal pharmacological treatment to prevent the formation of these complexes.

As the use of penicillinase has proved to be clinically disadvantageous and as it is, according to current knowledge, without pharmacological foundation, this mode of treatment is unknown in the current literature and in clinical practice.

As the development and occurrence of allergic symptoms in susceptible individuals are independent of the dose, β-lactam antibiotics are contraindicated in these patients.

Apart from the above-mentioned patient group, β-LABs can be used alone or in combination with other antimicrobial drugs for most bacterial diseases occurring in man, mostly with curative results.

Still, all individuals receiving therapeutic doses of these drugs exhibit microbiological side effects in the normal bacterial flora of the mouth, upper airways, gastrointestinal tract, urinary tract, genitals and skin.

In the present patent application, microbiological side effects of β-LABs refer to their undesired effects on the normal bacterial flora of the body, these effects being due to the clinical antimicrobial properties of these drugs.

The microbial side effects of β-LABs, as well as those of other classes of antibiotics, may be subclinical, i.e, giving rise to no perceptible symptoms, or they may be manifested as mild or even fatal symptoms. Examples of mild side effects are the familiar penicillin diarrhoea and mucosal yeast infection while the fatal side effects include severe colitis caused by broad-spectrum cephalosporin or carbapenem and systemic fungal infection encountered in immunosuppressed patients.

The above are examples of superinfection, that is, the development of a new microbial disease in conjunction with antibiotic therapy, the causative agent of the new infection being different from that of the original condition. Superinfections are relatively common but potentially very dangerous because the causative microorganisms, such as the enterobacteria, bacteria of the genus Pseudomonas, staphylococci and many microscopic fungi, are often highly resistant to currently available antimicrobial drugs.

Superinfections are most common in the bowel, especially in the colon the lumen of which contains the largest concentration of the normal bacterial flora of the body. The latter fact can be appreciated when considering that up to 50% of the dry weight of the faeces may consist of intestinal bacteria. In contrast to the large intestine, the small intestine is, with the exception of its very distal end, devoid of bacteria because of bacteriolytic enzymes secreted by the small intestine.

The function of the above-mentioned physiological bacterial flora is, in addition to contributing to the production and normal absorption of many trace substances essential to man, to occupy potential sites of growth of pathogenic microorganisms and to excrete chemical agents inhibiting the growth of such microorganisms.

Regarding β-LABs, their adverse microbiological effects in the intestines are due to oral or parenteral administration bringing a pool of the particular antibiotic into contact with the physiologically beneficial intestinal bacterial flora. In this way, β-LABs destroy such components of the normal bacterial flora that are sensitive to their action, thus increasing the relative amount of bacteria resistant to these drugs. This leads to disruption of the fundamental intestinal microbial ecology and creation of favourable circumstances for the multiplication and growth of resistant pathogenic microorganisms, such as the common opportunistic species *Clostridium difficile* (Sawa et al. 1985).

The higher the doses and the longer the period of treatment, the greater the risk of superinfection. Of all antibiotics, the probability of superinfections is greatest with broad-spectrum β-LABs, especially when administered in combination with other broad-spectrum antibiotics (Sande et al. 1990). It is noteworthy that the risk of superinfections exists even in the case of parenteral administration of β-LABs and even if only a minor amount of the antibiotic were expected to diffuse into the gut.

In many cases, the risk of microbiological side effects in the intestines and elsewhere in the body prevents continuation of antimicrobial therapy for a sufficient period of time. It also sets limits to single doses and total 24-h dosage.

The latter problem has been partly overcome in oral therapy by the use of preparations which are optimally absorbed from the intestines. Thus, amoxicillin (6), with its better absorption profile, is usually preferred over ampicillin (3) although the two have identical antibacterial spectra.

Ampicillin has been further derivatised into prodrug forms such as bacampicillin (4) and pivampicillin (5) (U.S. Pat. No. 3,488,729). These esters of ampicillin have no antimicrobial effect in the intestine. Nevertheless, when administered orally they are almost completely absorbed from the intestine after which they are hydrolysed in the systemic circulation back to ampicillin. The therapeutic effect of bacampicillin and pivampicillin is based exclusively on the antimicrobial activity of the ampicillin liberated from its ester precursor.

Some bacteria of the normal colonic flora have been found to be able to degrade some of the β-LABs, including ceftriaxon (43) and cefixime (48), in vivo (Sawa et al. 1985).

Patent document WO 88/07865 presents an approach whereby colonic bacteria capable of degrading some of the β-LABs in vitro are isolated from human faeces, cultured in vitro and processed into an orally administered pharmaceutical preparation containing these bacteria. This approach is claimed to reduce the adverse effects of β-LABs on the normal bacterial flora of the gut. The method is based on live bacteria with a characteristic ability to secrete β-lactamase in vitro.

Provided that the bacteria in question can be protected against the digestive action of gastric and intestinal juices on their way to the large intestine, the method can no doubt be used to increase the count of said bacteria in the large intestine where they already occur in physiological numbers. However, the adverse effects of concomitant β-LAB therapy on the intestinal bacterial flora are not necessarily reduced through the introduction of β-LAB-resistant intestinal bacteria. On the contrary, an increase in the relative number of β-LAB-resistant intestinal bacteria and their independent proliferation causes a typical situation predisposing the intestine to superinfections. The situation becomes further aggravated as the concomitantly administered β-LAB destroys those organisms of the normal flora that are sensitive to the antibiotic.

The mechanism of action of the enzyme proteins and the degradation in vivo of the β-LAB referred to in the present invention can both be demonstrated unambiguously, which is not the case with patent document WO 88/07865. As a matter of fact, ceftriaxon, the antibiotic used in the application examples of the latter invention, is known to be degraded to inactive metabolites by the intestinal flora in vive even without the addition of intestinal bacteria as proposed in said publication (Therapeutic Drugs 1991).

Thus, the approach presented in patent document WO 88/07865 alters the ecological relationships among the intestinal microbes, whereas a solution according to the present invention specifically prevents effects on the intestinal flora. The solution presented in patent document WO 88/07865 does not take into account the use of an isolated β-LAB-degrading enzyme or the fact that such an enzyme can be isolated even from other microorganisms than bacteria (fungi and algae) and also from mammalian cells. Even production using genetic engineering is possible. Furthermore, it is technically simpler to make, for instance, an enteric preparation of the enzyme than a corresponding preparation of live microbes. The doses, activities, purity, etc. of the enzyme proteins can be unambiguously measured and standardised.

The approaches so far presented have not been able to reduce the common β-LAB-associated problem of microbiological side effects, which via the intestines affect the entire body. The ever increasing use of β-LABs in general, and of broad-spectrum β-LABs in particular, in antibacterial therapy has aggravated this problem year by year on both individual and population level. The shift towards broader-spectrum antibiotics is due to the fact that antibiotic-resistant bacterial species and strains are increasingly encountered in the most commonplace infections.

The main mechanism by which certain pathogenic bacteria develop a resistance to β-LABs is the selection of β-lactamase-producing bacteria in the patient undergoing treatment.

β-lactamases are a structurally heterogeneous group of enzymes which share the ability to hydrolyse the β-lactam ring of β-LABs at the cyclic amide bond, thus cleaving the β-lactam ring and destroying the antimicrobial properties of the molecule in question.

Microbial β-lactamases (EC 3.5.2.6) are called penicillin amido-β-lactam hydrolases. According to the substrate most actively broken down by particular β-lactamases, these enzymes have also been called penicillinases (U.S. Pat. No. 2,982,696) or cephalosporinases. Dehydropeptidases (EC 3.4.13.11) are β-lactamases with a characteristic ability to specifically hydrolyse the β-lactam ring of carbapenems. They can be isolated only from mammalian cells (Kropp et al. 1982).

β-lactamases catalyse the conversion of penicillins specifically into corresponding penicilloic acids, of cephalosporins into corresponding cephalosporanoic acids and of carbapenems and monobactams into corresponding compounds with an open β-lactam ring.

The known β-lactamases exhibit a broader spectrum of hydrolytic activity than do the amidases (p. 3, lines 7–16). The known amidases are able to hydrolyse at least the following compounds: 1–3, 23, 24, 29, 30 and 33. The known β-lactamases, however, are able to hydrolyse every one of the substrates listed (1–50).

Contrary to the β-lactamases, amidases have not given rise to clinical problems in the form of bacterial resistance in conjunction with β-LAB therapy.

The present invention is aimed at reducing the microbiological problems encountered in β-LAB therapy by preventing the microbiological side effects caused by oral and parenteral administration of β-LABs.

β-LAB therapy is traditionally carried out according to the principle of systemic drug action irrespective of whether the infection itself is systemic or local (e.g. an inflamed rash). Local application to the skin has not been accepted because of the risk of sensitisation.

However, β-LABs introduced into the digestive tract are not locally sensitising.

During recent years, most cases of gastritis and peptic ulcers have been shown to be caused by *Helicobacter pylori*, a bacterium which infects the mucosa of the upper digestive tract. Eradication of this organism by antimicrobial therapy has proved more effective than any of the previous treatments for the above conditions. Successful elimination of *H. pylori* has brought lasting results in these diseases.

The most common form of treatment today is oral, high-dose, 14-day administration of amoxicillin (6) or alternatively tetracycline in combination with nitroimidazole antibiotic and bismuth salt, known as triple therapy (Rauws and Tytgat 1990). However, the treatment is associated with a high frequency of side effects which often lead to discontinuation of therapy. The bismuth salts, which are used for periods of 4–6 weeks, sometimes cause central nervous system side effects which may be severe. These effects may also be encountered in association with the use of nitroimidazole antibiotics.

The results reported on treatment with amoxicillin alone (Rauws et al. 1988) have been as good as those with triple therapy. In these studies, the duration of treatment (28 days) was much longer than that applied in conventional amoxicillin therapy (7–10 days), which increased the risk of microbiological side effects.

Irrespective of whether the above drugs are used alone or in combination, the outcome of treatment aimed at eradicating *H. pylori* is currently quite uncertain, as the risk or an actual occurrence of side effects precludes a treatment of sufficient duration and intensity. As a result, *H. pylori* can be found again on the gastric mucosa of half the patients four weeks after the end of treatment (Iserhard et al. 1990).

According to studies in vitro, *H. pylori* is sensitive to the following β-LABs besides amoxicillin: 1, 3, 8, 30, 34, 40, 48 and 49. Among the latter, 30, 34, 40 and 49 are broad-spectrum β-LABs reserved for parenteral use in hospitals, and their oral administration is unknown in clinical practice. Penicillin G (1) is sensitive to the action of acids and decomposes rapidly in the stomach. Being more readily absorbed than ampicillin (3), amoxicillin has been used for eradication of *H. pylori*. Bacampicillin (4), too, has been used in therapeutic trials, which presents an opportunity to evaluate the role of the local effect of β-LABs, in this case amoxicillin, in *H. pylori* eradication therapy.

Since bacampicillin, even at high ampicillin concentration (which, owing to the prodrug nature of bacampicillin, can only exert a systemic influence), has not shown any appreciable antimicrobial effect on *H. pylori* and since the antibacterial spectra and systemic pharmacokinetics of ampicillin and amoxicillin are almost identical (Hirschl et al. 1987), it can be concluded that amoxicillin also lacks appreciable systemic effect on this bacterial species.

Therefore, the positive results gained with oral amoxicillin in the eradication of *H. pylori* may be explained as a topical effect of this β-LAB.

The present invention is also aimed at reducing the microbiological side effects of β-LABs in cases where the antimicrobial therapy is directed locally to the upper digestive tract, i.e. to the esophagus, stomach and duodenum, which may contain pathogenic bacteria sensitive to the β-LABs employed.

The present invention offers significant alleviation of the aforementioned problems encountered in the β-LAB treatment of bacterial diseases and caused by the microbiological side effects of said drugs.

Oral pharmaceutical preparations with a programmed delivery pattern refer to monolithic (in the form of one particle) or multiparticular dosage forms characterised by the release of the comprised active ingredient in a certain, desired section of the digestive tract having been programmed in advance into the structure of the preparation.

Monolithic solutions include, i.a., packing of the drugs into various insoluble matrices from the pores of which the active ingredient dissolves at a uniform rate as the preparation moves along the digestive tract ("matrix dosage form"). In a solution resembling the above, the active ingredient is released through a hole in the insoluble coating of the monolith, e.g. a tablet, as a result of osmotic pressure when a water-absorbing inert mass packed into the monolith swells ("osmotic pump device"). Multiparticular solutions include granules coated with a gastric juice-resistant layer, which is, e.g. when the pH rises, broken down in a desired section of the intestine, releasing the comprised active ingredient ("enteric coated granules"). A similar principle is used in the case of gastric juice-resistant liposomes into which a drug can be packed for the same purpose as in the above solutions.

The present invention involves the use of orally administered enzymes for breaking down the adverse β-LAB pool, which inevitably accumulates in the intestines in conjunction with β-LAB therapy, into compounds with little or no antibacterial activity in the gut.

β-lactamases and/or amidases or active fragments (it is a general property of enzymes that they can be truncated to a certain degree without loss of activity; it is prerequisite that the catalytic site of the enzyme remain intact, however) of any of these, specifically isolated for the purpose, can, by incorporating them into structurally and functionally defined pharmaceutical preparations with a programmed delivery pattern, in conjunction with β-LAB therapy, be rendered to be released preferably in the duodenum and/or the small intestine and/or the large intestine and thus be brought, as programmed, into contact with said β-LAB pool in a desired section of the alimentary canal.

Oral preparations of said enzymes can be delivered to the gut also by protecting them from gastric juices by means of compounds which inhibit hydrochloric acid and/or pepsin. Hydrochloric acid secretion can be inhibited e.g. by histamine $H_2$ receptor blocking agents or the so-called proton pump inhibitors, such as omeprazole. Pepsin can be inhibited for instance with pepstatin. The enzymes can also be protected from gastric juice by neutralising the hydrochloric acid with an antacid; as the pH rises, the activity of pepsin will also be inhibited.

By the use of amidases released by the above means in the desired section(s) of the alimentary canal, penicillins can be converted into 6-APA and cephalosporins into 7-aminocephalosporanic acids (7-ACA or compounds with a 7-ACA nucleus) with no appreciable antimicrobial properties.

By the use of β-lactamases released by the above means in the desired section(s) of the alimentary canal, penicillin can be converted into corresponding penicilloic acids and cephalosporins into corresponding cephalosporanoic acids. Carbapenems and monobactams are likewise converted into corresponding compounds with an open β-lactam ring. The above compounds exhibit no antimicrobial activity.

The advantages and benefits of the invention are produced using the procedures presented as distinguishing in the appended patent claims.

Application of the present invention to the prevention of the microbiological side effects of β-LABs has the following significant advantages over previous state of the art:

Since the antimicrobial activity of the unabsorbed fraction of a dose of an oral, incompletely absorbable β-LAB, which has microbiological side effects in the normal bacterial flora of the gut, can be completely or partly eliminated less microbiological side effects, such as antibiotic diarrhoea and mucosal yeast infections, which impair the quality and efficacy of therapy, are produced in conjunction with conventional oral G-LAB therapy, such as the treatment of commonplace respiratory and skin infections, compared with current clinical practice.

higher single and 24-hour doses than previously can be adopted, as required, in oral β-LAB therapy. Also the total duration of the treatment can be extended, which is a great asset, for instance, in the treatment of gastrointestinal diseases (gastritis and peptic ulcers) caused by *H. pylori*.

unabsorbable β-LABs, the use of which has been limited to parenteral therapy, can for the first time be considered for oral therapy in the topical treatment of bacterial infections of the upper digestive tract, including various degrees of gastric mucosal infection caused by *H. pylori*.

In view of the above-related benefits which increase the area of use of β-LABs, gastrointestinal conditions caused by *H. pylori* can be treated more effectively and more fully curative results can be reached by using only one β-LAB, still producing less microbiological side effects than previously.

Using a single β-lactam antibiotic naturally avoids the side effects produced by the other antimicrobial agents included in combination therapy. Because of the risk of side effects, antimicrobial therapy of gastrointestinal diseases caused by *H. pylori* has so far been applied only to the treatment of peptic ulcers, not to gastritis, let alone to asymptomatic carries of *H. pylori*.

The present invention allows single β-LAB therapy to be extended to the two latter groups, in which, as well as in the first-mentioned patient group, such causal therapy can be expected to reduce the requirement for symptomatic medication.

Even in the case of parenterally administered β-LABs, part of the dose reaches the gut lumen, either by excretion in the bile or by diffusion through the intestinal wall, causing microbiological side effects in the normal bacterial flora.

As above, the antimicrobial properties of this β-LAB pool can be completely or partly removed by application of the present invention, thus decidedly reducing these side effects in conventional parenteral β-LAB therapy, e.g., in the treatment of serious systemic infections requiring very high 24-hour dosages in the form of divided doses or continuous infusion and often employing combination therapies involving a great number of side effects, and thereby improving the outcome of treatment.

It should be noted that the microbiological inactivation of the β-LAB accumulated in the gut only takes place after the compound in question has exerted its therapeutic effect.

the compounds derived from inactivated β-LABs are nontoxic.

the above compounds are absorbed much less from the intestine than are their parent compounds.

Thus, the aforementioned benefits gained by application of the invention are available without any impairment of the therapeutic properties of the β-LABs employed and without any increase in clinical toxicity or allergenicity over that conventionally associated with the use of the parent compound.

The chemical development of β-LABs, aimed at producing new molecular constructions with broader antimicrobial spectra and better resistance to β-lactamase, has unfortunately brought along a simultaneous increase in the risk of side effects. Regarding long-range changes in the entire field of antibiotic therapy on a population basis, bacterial mutation-induced resistance to β-LABs and other antibiotics has long been a grave concern in clinical practice. Many β-LABs and other antimicrobial agents, which were efficacious only a couple of years ago, are rapidly losing their effect and thereby their significance in the treatment of many diseases caused by bacteria formerly sensitive to these drugs. This has been the inevitable result of the explosive increase in the, often indiscriminate, use of antibiotics.

Regarding application of the present invention to antibiotic therapy using β-LABs and in view of what has been said above, it should be emphasised that the proposed applications tend to lower the doses and reduce the number of different β-LABs and, indirectly, of other antibiotics used in therapy.

As the antibiotic is inactivated prior to its reaching the large intestine, application of the invention does not cause antibacterial effects altering the ecology of the large intestine. In this context, the invention can be considered to have the general benefit that its application does not leave room for the selection of new antibiotic-resistant strains of bacteria.

Indeed, the most important general benefit of the invention can be considered to be the fact that its application does not promote selection of new antibiotic-resistant, pathogenic strains of bacteria.

Procedures required to produce the effect claimed for the invention have been referred to above. The applicability of the invention can be further improved in the following way:

The hepatopancreatic duct, which in the adult enters the duodenum some 10 to 15 cm distally from the pylorus, secretes, especially after meals, an inactive proenzyme known as trypsinogen, which the enterokinase in the gut wall rapidly converts into trypsin, an active enzyme which digests the proteins in the chyme. Trypsin also activates other digestive enzymes responsible for splitting proteins; it further activates trypsinogen itself in a process known as autocatalysis.

The effect of the trypsin on the chyme is greatest in the duodenum and in the proximal section of the small intestine. The enzyme loses its activity gradually towards the distal end of the small intestine. Trypsin secretion is minimal during fasting.

As the proteolytic action of active trypsin and other digestive enzymes also affects any orally administered β-lactamases and amidases used in applications of the present invention, especially if the latter enzymes are programmed to be released already in the duodenum, it is sensible to inactivate the duodenal trypsin by means of trypsin inhibitors.

Known trypsin inhibitors include α1-antitrypsin, pancreatic trypsin inhibitor (PSTI) (FI 880017), aprotinine (U.S. Pat. No. 2,890,986, EP 0 420 600 A2), trypstatin (EP 0 384 559), α2-macroglobulin, soybean trypsin inhibitor and egg white trypsin inhibitor. Each of these are available commercially. They are all proteins in chemical structure.

In an application of the present invention, they are incorporated into pharmaceutical preparations with a programmed delivery pattern and brought to the desired site(s) of action through oral administration either separately from β-lactamase and/or amidase or in the same preparation with these enzymes.

Naturally, compounds suppressing or inhibiting other digestive enzymes (pepsin, etc.) can also be used as required.

The function of the invention will be described below with examples of practical applications. The medical usage, methods and preparations based on the invention are not limited to these examples, however.

EXAMPLE 1

The invention is applicable, for instance, to topical antimicrobial therapy for peptic ulcers and symptomatic or asymptomatic gastritis, caused by H. pylori, as follows:

The β-LAB used in the example is ampicillin (VII)

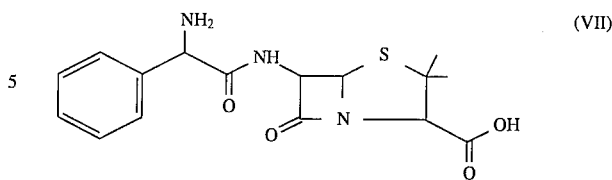

to which H. pylori is known to be sensitive in vitro, the minimal concentration inhibiting 90% of the bacteria (MIC90) being 0.03 μg/ml (Lambert et al. 1986).

We know that in man a total of only 30–40% of an oral dose of ampicillin is absorbed into the systemic blood circulation, with the rest remaining in the intestine. The absorption takes place within about two hours, that is, before the antibiotic reaches the mid-portion of the small intestine. A major part of the dose is excreted unchanged in the faeces. The halflife of ampicillin in the lo systemic circulation is approx. 1.5 h.

In the example, ampicillin is administered orally in the conventional manner as three or four daily doses of 250–1000 mg each. Preferably, granules 3–5 mm in diameter are taken into an empty stomach, in which case the agent is retained in the stomach for 30–60 min. During this period, when the granules dissolve, an ampicillin concentration $10^4$–$10^5$ times the MIC for H. pylori is maintained on the gastric mucosa. We know that with β-LABs two or three 30–60 min periods daily during which the antibiotic concentration is in excess of the MIC is sufficient to produce a full bactericidal effect. This condition is evidently fulfilled in all mucosal layers in the present example, as the gastric (and duodenal) mucosa is only about 1 mm in thickness.

In accordance with the distinctive features of the invention, the ampicillin which enters the duodenum through the pylorus exerts its local therapeutic effect on the mucosa after which it is broken down into 6-APA (IV), which has little microbiological activity, or into the penicilloic acid corresponding to ampicillin (VI), which has no antimicrobial activity at all. This takes place prior to the unchanged ampicillin coming into contact with the physiological bacterial flora of the distal small intestine and the large intestine.

The ampicillin is best broken down into VI by means of type I-β-lactamase (abbreviated to BC I in this patent application) produced by the 569/H/9 strain of Bacillus cereus. The isolation, purification and biochemical properties of BC I have been documented (Davies and Abraham 1974), and the enzyme is available commercially (Sigma, Mo., USA).

The ampicillin is best broken down into 6-APA by means of ampicillin acylase (ampicillin amidase) (abbreviated to PMAA in this patent application) produced by the IFO 12020 strain of Pseudomonas melanogenum. The isolation, purification and biochemical properties of PMAA have been documented (Kim and Buyn 1990).

Enzyme activities are expressed in units (U). 1 U of enzyme breaks down 1 μM of its substrate in 1 min.

With ampicillin as its substrate, BC I has a specific activity of 2000 U/mg enzyme protein at a temperature (37°) and pH (4.5–7.0) corresponding to conditions in the duodenum and small bowel. This means that 1 mg of BC I breaks down 680 mg of ampicillin into the corresponding penicilloic acid per minute.

The corresponding specific activity of PMAA is 1000 U/mg, and thus 1 mg of this enzyme protein breaks down 340 mg of ampicillin into 6-APA per minute in the same conditions.

BC I or PMAA, depending on whether one desires the ampicillin inactivated into 6-APA or VI, is administered orally in the form of a pharmaceutical preparation with programmed release of the active ingredient in the duodenum, where the enzyme comes into contact with the ampicillin simultaneously present in this part of the gastrointestinal tract.

The enzymes are protected against the action of the acid gastric juice by the so-called enteric coating technique (Chambliss 1983) combined with microcapsulation (Madan 1978). These techniques yield particles with a diameter of 1.0–2.5 mm. When such granules are administered by the mouth, their gastric retention time is in the same order as that of the ampicillin administered according to the present example, and thus the enzyme and the ampicillin can be administered at the same time.

When polyvinyl acetate (Colorcon®) is used to coat the protein granules constituting an embodiment of the invention, said coating is dissolved rapidly (in 5–15 min) when the ambient pH exceeds 4.7. Since such pH is typical of the intestine from the very proximal duodenum onwards, the active ingredient, BC I or PMAA, is liberated in this desired section of the gut and mixed with the ampicillin entering simultaneously with it through the pylorus.

Since said enzymes are, after their entry in the duodenum, in the sphere of influence of the pancreatic proteolytic enzymes, it is rational to protect them with a trypsin-inhibiting protein, as the inactivation of trypsin also prevents the activation of other proteolytic enzymes secreted by the pancreas.

In a situation such as in the present example, with the preparations being ingested into an empty stomach, the digestive tract is in a fasting state, in which the secretion of digestive enzymes, e.g. trypsin, is only a fraction (a few milligrams per hour) of that taking place during a full meal (100–200 mg/h).

Of the many suitable trypsin-inhibiting proteins, for instance the soybean trypsin inhibitor (type II-S, Sigma) can be used. Having come into contact with trypsin, each milligram of this protein rapidly inactivates 1.5–2.5 mg of trypsin.

If the above-described enteric coated granules, administered as a single dose according to the example, comprise 100 mg of soybean trypsin inhibitor, the amount of this protein liberated in the duodenum is sufficient to inactivate many times over the trypsin present in this intestinal section.

If the above-described enteric coated granules, administered as a single dose according to the example, comprise 10 mg (10,000 U) of PMAA, the amount of this enzyme, which arrives in the duodenum simultaneously with the ampicillin and is able to break down ampicillin into 6-APA, is sufficient to render 100 g of ampicillin microbiologically inactive within a 30 min period after its release.

Correspondingly, if the above-described enteric coated granules comprise 5 mg of BC I in a single dose, the amount of this enzyme, which arrives in the duodenum simultaneously with the ampicillin and is able to break down ampicillin into penicilloic acid, is likewise sufficient to render 100 g of ampicillin microbiologically inactive within a 30 min period after its release.

Examples of the doses and compositions of the pharmaceutical preparations which form embodiments of the present invention are given below.

| | | |
|---|---|---|
| a) | 500 mg of granules (approx. 0.8 ml) contain: | |
| | BC I enzyme protein | 5 mg |
| | soybean trypsin inhibitor | 100 mg |
| | saccharose | 200 mg |
| | flavouring and colouring | 5 mg |
| | polyvinyl acetate (enteric coating) | 190 mg |
| b) | 500 mg of granules contain: | |
| | PMAA | 10 mg |
| | soybean trypsin inhibitor | 100 mg |
| | saccharose | 195 mg |
| | flavouring and colouring | 5 mg |
| | polyvinyl acetate (enteric coating) | 190 mg |

A dose corresponding to example a or b may be enclosed in a gelatin capsule, which instantly dissolves in the stomach, or it may be administered as such, e.g. from a single-dose sachet, simultaneously with ampicillin.

EXAMPLE 2

In cases where the part of a dose of conventional oral β-LAB which would be normally absorbed from the intestine into the systemic circulation is not wanted broken down, the enzymatic splitting can still be carried out on the unabsorbed part of the dose. This application of the invention is useful in most areas of conventional oral β-LAB therapy: commonplace bacterial infections of the ears, paranasal sinuses, pharynx, bronchi, lungs, urinary tract, skin, etc., when treated with compounds 2–6, 9, 10, 13–18 or 23–29.

As the microbiological action of the above oral β-LABs can be eliminated successfully through an application of the present invention as late as 3–6 h after administration, the splitting of the β-LAB can be carried out slowly, over one to three hours, allowing very economical doses of β-lactamases or amidases to be used.

In this application, the granules containing the active enzymes are coated with methacrylic acid polymer (Eudragit SR). The latter dissolves when the ambient pH exceeds 7.0, and thus the enzyme constituting the active ingredient is not liberated until the granules reach the distal small intestine. This application can be combined, for instance, with amoxicillin therapy for the eradication of *H. pylori*, a treatment which has so far been rendered more or less ineffective by the microbiological side effects which seriously limit dosage and the duration of treatment.

Examples of the doses and compositions of the pharmaceutical preparations which form embodiments of the present invention are given below.

| | | |
|---|---|---|
| c) | 500 mg of granules contain: | |
| | BC I enzyme protein | 5 mg |
| | soybean trypsin inhibitor | 150 mg |
| | saccharose | 150 mg |
| | flavouring and colouring | 5 mg |
| | methacrylic acid polymer (enteric coating) | 190 mg |

100 mg of the granules are taken, e.g. together with a conventional dose of amoxicillin, ampicillin, penicillin V, etc.

| | | |
|---|---|---|
| d) | 500 mg of granules contain: | |
| | PMAA | 10 mg |
| | soybean trypsin inhibitor | 150 mg |
| | saccharose | 145 mg |
| | flavouring and colouring | 5 mg |
| | methacrylic acid polymer (enteric coating) | 190 mg |

100 mg of the granules are taken, e.g. together with a conventional dose of ampicillin, penicillin V or cephaloglycin.

EXAMPLE 3

Applications of the invention can also be used to render unabsorbable β-LABs, that is, parenterally administered penicillins, cephalosporins, carbapenems and monobactams microbiologically inactive. The area of application covers all β-LAB therapies in which the parenterally administered antibiotic diffuses through the gut wall or is excreted in bile, forming an intestinal pool of antibiotic which causes microbiological side effects, as well as topical treatment of the upper digestive tract in which a mainly parenteral β-LAB is administered orally.

Cephalothin (VIII) and imipenem, i.e. N-formidoyl thienamycin, (IX) serve as examples of this area of application of the invention:

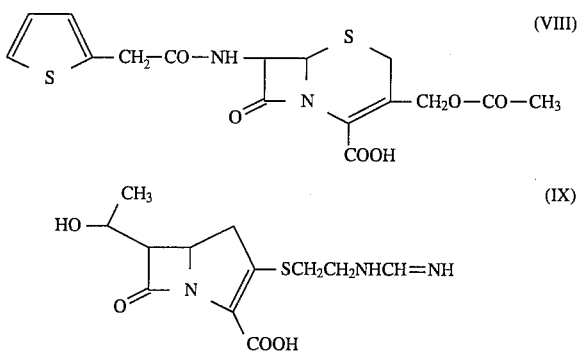

It is known that only 1–3% of an oral dose of these parenteral β-LABs is absorbed. $H.$ $pylori$ is sensitive to imipenem and cephalothin in vitro (MIC90=0.2 µg/mi), which makes imipenem and cephalothin well suited for eradication of $H.$ $pylori$ by oral administration according to the present invention.

Cephalothin can be broken down into 7-ACA, e.g. with amidase (Cole 1969). Likewise, cephalothin can be broken down into the corresponding cephalosporanoic acid with BC I, but even greater activity with this antibiotic is exhibited by the commercially available cephalosporinase produced by strain 214 of $Enterobacter$ $cloacae.$ The specific activity of the latter β-lactamase with cephalothin is 50 U/mg in conditions corresponding to the lower sections of the gastrointestinal tract.

Imipenem can be broken down into the corresponding compound with an open β-lactam ring by means of the dehydropeptidase I (DHP I) enzyme isolated from mammalian cells. Porcine renal DHP I, for example, has a specific activity of 90 U/mg with imipenem as substrate (Kropp et al. 1982).

According to the invention, imipenem and cephalothin are best used as single doses of 250–1000 mg for the eradication of $H.$ $pylori$ by local treatment targeted at the gastric and duodenal mucosae. As the antimicrobial action of these two orally administered antibiotics does not reach the normal bacterial flora of the gut until 3–6 h after administration, when the antibiotic enters the main area of distribution of the normal intestinal flora, this entire period is available for the enzymatic inactivation of imipenem or cephalothin.

This time can be best availed of by incorporating into the same dose with the antibiotic preparation enteric coated granules which release an imipenem- or cephalothin-inactivating enzyme at various pHs in the intestine.

This can be done by simultaneous use of granules coated with either polyvinyl acetate (examples a and b), methacrylic acid polymer (examples c and d) or cellulose acetate phthalate (CAP, Eastman Kodak), which release the active ingredient in different parts of the intestine: in the duodenum (when the pH exceeds 5.5), in the duodenum and the small intestine (when the pH exceeds 6.0) and in the distal small intestine (when the pH exceeds 7.0).

A single dose of enteric coated granules made in the way described above, containing as the active ingredient 10 mg (500 U with cephalothin as substrate) of β-lactamase derived from $Enterobacter$ $cloacae,$ is sufficient to break down a 500 mg dose of cephalothin within the small intestine before the beginning of the large intestine even if only one-hundredth of the enzyme protein were active.

Correspondingly, a single dose of enteric coated granules containing 10 mg (i.e. 900 U with imipenem as substrate) of DHP I is sufficient to break down approximately one gram of imipenem within the small intestine even if only one-hundredth of the enzyme protein were active.

The following examples describe the degradation of a β-lactam antibiotic into inactive form in the intestine in vivo.

EXAMPLE 4

Use of β-lactamase to break down a β-lactam antibiotic in the rat intestine in vivo:

β-lactamase-induced degradation of ampicillin, which is a β-lactam antibiotic, in the rat intestine in vivo was investigated. Ampicillin was injected into the duodenum, followed by injection of β-lactamase and trypsin inhibitor, or plain vehicle. After 20 min the contents of the small intestine was absorbed in a paper disk. The disk was then transferred onto agar containing an ampicillin-sensitive $Staphylococcus$ $aureus$ culture in order to find out whether the small intestine still contained active ampicillin.

The test animals were male Sprague-Dawley rats (Alab, Sweden) weighing 432–471 g. The animals were kept in groups of five in cages with free access to water and food pellets. A standard 12:12 h light-dark cycle (lights on from 6 am to 6 pm) was applied. The rats were fasted for 24 h prior to the experiment.

The rats were anaesthetised with chloral hydrate (3.6 g/100 ml) at an i.p. dose of 0.85 ml/100 g. The peritoneum was cut in midline exposing the stomach and intestines. The pylorus and duodenum (at 40 mm from the pylorus) were ligated. Sodium ampicillin (A-PEN, Orion Corporation, 10 mg in 0.10 ml of sterile water titrated to pH 5.5) was injected into the duodenum at a point 5 mm from the pylorus. Five minutes later either 500 µg β-lactamase (type I: $Bacillus$ $cereus,$ Sigma) and 500 µg trypsin inhibitor (type II-S, soybean, Sigma) in 0.10 ml of sterile water titrated to pH 5.5 or 0.10 ml of water was injected into the duodenum at the same site. The exposed peritoneum and intestine were irrigated with a swab wetted with physiological saline to prevent drying. Twenty minutes later a 150 µl sample of the duodenal contents was drawn with an injection needle at a point 10 mm from the duodenal ligation. The sample was injected into a test tube containing 2 ml of water, and the tube was immediately placed in a 100° C. water bath for 5 min to stop the enzyme reaction. After the tube had cooled to room temperature, 2 mi of water was added and the tube was agitated using a Vortex mixer. A 150 µl sample was absorbed in a disk of paper (diameter 12.7 mm), which was then placed on an agar plate (bottom: Medium I Difco 6 ml; surface: Medium I Difco 4 ml) the surface of which was coated with ampicillin-sensitive *Staphylococcus aureus* (ATCC 6538p; a concentrated suspension was diluted 1:10, and 8 ml of the dilution was used on 100 ml of agar). Each agar plate also received a standard disk containing ampicillin diluted to the same concentration as in the test solution. The plates were incubated at 37° C. for 18 h, and the inhibition zones around the disks were measured.

Table 1 presents the results for each agar plate. The effect of β-lactamase is evident. The standard disks and the disks containing samples from rats which had received only ampicillin showed distinct inhibition of bacterial growth, whereas the disks with samples from rats which had received β-lactamase and trypsin inhibitor in addition to ampicillin did not inhibit bacterial growth.

The results indicate that unabsorbed β-LAB can be inactivated with β-lactamase in an intestinal environment in vivo.

TABLE 1

Diameters of inhibition zones around the paper disks.
A = ampicillin; B = β-lactamase + trypsin inhibitor

| Rat | Sample | Inhibition zone diameter (mm) | |
| --- | --- | --- | --- |
| | | Test | Standard |
| 1 | A + B | — | 40 |
| 2 | A | 34 | 40 |
| 3 | A + B | — | 40 |
| 4 | A | 34 | 40 |
| 5 | A + B | — | 41 |
| 6 | A | 34 | 41 |
| 7 | A + B | — | 39 |
| 8 | A | 33 | 39 |
| 9 | A + B | — | 42 |
| 10 | A | 33 | 42 |
| 11 | A + B | — | 36 |
| 12 | A | 31 | 36 |
| 13 | A + B | — | 35 |
| 14 | A | 30 | 35 |
| 15 | A + B | — | 34 |
| 16 | A | 28 | 34 |
| 17 | A + B | — | 33 |
| 18 | A | 29 | 33 |
| 19 | A + B | — | 33 |
| 20 | A | 27 | 33 |

EXAMPLE 5

Use of amidase to break down a β-lactam antibiotic in the rat intestine in vivo:

Analogously with Example 4, 10 mg of sodium ampicillin in 0.10 ml of sterile water titrated to pH 5.5 was injected into the rat duodenum. Further, 5 min later 100 U of amidase (ampicillin acylase; Department of Biotechnology, Research & Development Center, KOSCO, Soul, South Korea) derived from the IFO 12020 strain of *Pseudomonas melanogenum* and 500 μg of trypsin inhibitor (type II-S, soybean, Sigma) was injected into the duodenum at the same site. The control rat only received the 10 mg ampicillin solution in 0.10 ml of sterile water (pH 5.5) followed 5 min later by an equal volume of plain sterile water. The experiment was then continued following the procedure in Example 4, with a final incubation of the disks on agar plate for 18 h. The results indicate that unabsorbed β-lactam antibiotic can be broken down by amidase in the intestine in vivo.

REFERENCES CITED

Patent documents:
EP 0 384 559
EP 0 420 600 A2
FI 59265
FI 880017
GB 1241 844
U.S. Pat. No. 2,890,986
U.S. Pat. No. 2,941,995
U.S. Pat. No. 2,982,696
U.S. Pat. No. 3,070,511
U.S. Pat. No. 3,150,059
U.S. Pat. No. 3,239,394
U.S. Pat. No. 3,488,729
U.S. Pat. No. 3,499,909
WO 88/07865
Other publications:
Chambliss WG (1983) Pharm Technol 7, 124.
Cole M (1969) Biochem J 115, 733.
Davies R, Abraham E (1974) Biochem J 143, 115.
Hirschl A et al. (1987) Wien Klin Wsch 14, 493.
Huber et al. (1972) In: Flynn E, ed. Cephalosporins and Penicillins. New York: Academic Press, 27.
Hyman AL (1959) JAMA 169, 593.
Iserhard R et al. (1990) Hepato-Gastroenterol 37, 38.
Kim DJ, Buyn SI (1990) Biochem Biophys Acta 1040, 12.
Korzybski T, Kurylowicz W (1961) In: Antibiotica. Jena: Veb G Fischer Verlag, 778.
Kropp H et al. (1982) Antimicrob Agents Chemother 22, 62.
Lambert et al. (1986) Antimicrob Agents Chemother 30, 510.
Madan PL (1978) Pharm Technol 2, 68.
Mandell GL, Sande MA (1990) In: Goodman and Gilman's, The Pharmacological Basis of Therapeutics, 8th Edition. New York: Pergamon Press, 1065.
Rauws EA et al. (1988) Gastroenterol 94, 33.
Rauws EA, Tytgat GNJ (1990) Lancet 335, 1233.
Sande et al. (1990) In: Goodman and Gilman's, The Pharmacological Basis of Therapeutics, 8th Edition. New York: Pergamon Press, 1018.
Sawa K et al. (1985) Chemotherapy (Tokyo) 33, Suppl. 6, 169
Therapeutic Drugs (1991), Dollery C, ed. Edinburgh: Churchill Livingstone, C 129.

I claim:

1. An oral pharmaceutical preparation with a programmed delivery pattern comprising a substantially pure β-lactam antibiotic-degrading compound.

2. The preparation according to claim 1 wherein the β-lactam antibiotic degrading compound is selected from a group consisting of β-lactamase, an amidase and an active fragment of β-lactamase or amidase.

3. The preparation according to claim 1 further comprising an effective amount of a β-lactam antibiotic.

4. The preparation according to claim 3 wherein the antibiotic is selected from a group consisting of ampicillin, cephalothin and imipenem.

5. The preparation according to claim 3 wherein the amount of β-lactam antibiotic is 250–1000 mg.

6. The preparation according to claim 1 further comprising a compound which inhibit trypsin, pepsin or any corresponding digestive substance to protect the β-lactam antibiotic-degrading compound from the digestive action of trypsin or an equivalent substance in the digestive tract.

7. The preparation according to claim 6 wherein the trypsin inhibiting compound is selected from a group consisting of α 1-antitrypsin, PSTI, aprotinine, trypstatin, α

2-macroglobulin, soybean trypsin inhibitor, egg white trypsin inhibitor and equivalent.

8. The preparation according to claim 1 wherein the β-lactam antibiotic degrading compound is enteric coated so that the preparation passes the stomach without releasing the compound; said preparation releasing the compound in duodenum, duodenum and small intestine and distal small intestine.

9. The preparation according to claim 8 wherein the coating is selected form the group consisting of polyvinyl acetate, methacrylic acid polymer and cellulose acetate phthalate.

10. An oral pharmaceutical preparation with a programmed delivery pattern consisting essentially of a β-lactam antibiotic degrading compound selected from a group consisting of β-lactamase, an amidase and an active fragment of β-lactamase or amidase.

11. A method of using a β-lactam antibiotic degrading compound or an active fragment thereof comprising preparing a pharmaceutical preparation, suitable for oral administration, which comprises at least a β-lactam antibiotic-degrading compound, such that by administering the preparation to a patient in need thereof the β-lactam antibiotic-degrading compound breaks down antibiotics containing a β-lactam ring into inactive or low-active forms in the esophagus, stomach, duodenum, small and large intestine of the digestive tract, thereby limiting the effect of the β-lactam antibiotic and reducing the adverse effects of these antibiotics.

12. The method of using a compound according to claim 11 wherein the β-lactam antibiotic-degrading compound is an enzyme or an active fragment thereof.

13. The method of using a compound according to claim 12 wherein the enzyme is selected from a group consisting of β-lactamase, an amidase and an active fragment of β-lactamase or amidase.

14. The method of using a compound according to claim 11 wherein the adverse effect of the antibiotic is reduced by breaking down superfluous antibiotic as it passes into the duodenum, small intestine or large intestine.

15. The method of using the compound according to claim 11 wherein the preparation further comprises a compound which inhibits trypsin, pepsin or any corresponding digestive substance thereby protecting the β-lactam antibiotic-degrading compound in the digestive tract.

16. The method of using the compound according to claim 11 wherein the β-lactam antibiotic, the preparation of the β-lactam degrading compound and the compound which inhibits trypsin or corresponding digestive substances are administered together or separately, at the same time or in succession in a desired suitable order.

17. The method of using according to claim 11 wherein the pharmaceutical preparation comprising the β-lactam antibiotic-degrading compound has a programmed delivery pattern.

18. A method for reducing the adverse effects of antibiotic therapy with a β-lactam antibiotic in the digestive tract comprising:

a) administering an effective amount of a β-lactam antibiotic-degrading compound which is liberated from a composition in the digestive tract;

b) administering an effective amount of β-lactam antibiotic which comes in contact with the β-lactam antibiotic degrading compound in the digestive tract; said antibiotic breaking down into an inactive or a low-active product.

19. The method according to claim 18 wherein the β-lactam antibiotic-degrading compound is selected from a group consisting of β-lactamase, an amidase and an active fragment of β-lactamase or amidase.

20. The method according to claim 18 wherein the β-lactam antibiotic is administered to treat bacterial gastric infections.

21. The method according to claim 18 wherein the β-lactam antibiotic is administered to treat gastric *Helicobacter pylori* infections.

* * * * *